United States Patent

Frickel et al.

(10) Patent No.: US 6,820,013 B1
(45) Date of Patent: Nov. 16, 2004

(54) METHOD AND DEVICE FOR THE ONLINE ANALYSIS OF SOLVENT MIXTURES

(75) Inventors: Hans Frickel, Muehltal (DE); Hanshelmut Itzel, Ober-Ramstadt (DE); Joachim Born, Seeheim-Jungenheim (DE)

(73) Assignee: Merck Patent GmbH, Darmstadt (DE)

( * ) Notice: Subject to any disclaimer, the term of this patent is extended or adjusted under 35 U.S.C. 154(b) by 84 days.

(21) Appl. No.: 10/168,578

(22) PCT Filed: Dec. 5, 2000

(86) PCT No.: PCT/EP00/12199

§ 371 (c)(1),
(2), (4) Date: Oct. 16, 2000

(87) PCT Pub. No.: WO01/48458

PCT Pub. Date: Jul. 5, 2001

(30) Foreign Application Priority Data

Dec. 23, 1999 (DE) .......................................... 199 63 561

(51) Int. Cl.[7] .............................................. G01N 31/00
(52) U.S. Cl. ............................. 702/25; 702/23; 702/27; 702/28; 702/30; 702/31; 702/32; 702/172
(58) Field of Search ....................... 702/23, 25, 27–32, 702/76, 77, 85, 87–91, 97, 172; 356/301; 250/339.067, 339.06–339.07, 339.09, 339.11, 339.12, 252.1

(56) References Cited

U.S. PATENT DOCUMENTS

| | | | | |
|---|---|---|---|---|
| 4,655,225 A | * | 4/1987 | Dahne et al. ................ 600/316 |
| 5,121,337 A | * | 6/1992 | Brown ......................... 702/28 |
| 5,121,986 A | * | 6/1992 | Rutz ........................... 356/133 |
| 5,242,602 A | * | 9/1993 | Richardson et al. ......... 210/745 |
| 5,311,445 A | | 5/1994 | White |
| 5,512,751 A | | 4/1996 | Murray, Jr. et al. |
| 5,652,653 A | * | 7/1997 | Alsmeyer et al. ........... 356/301 |
| 5,850,623 A | * | 12/1998 | Carman et al. ............... 702/28 |
| 5,870,185 A | * | 2/1999 | See et al. .................... 356/128 |
| 6,159,255 A | | 12/2000 | Perkins |
| 6,507,401 B1 | * | 1/2003 | Turner et al. ................ 356/436 |
| 6,623,977 B1 | * | 9/2003 | Farquharson et al. ....... 436/164 |

* cited by examiner

*Primary Examiner*—Marc S. Hoff
*Assistant Examiner*—Carol S. Tsai
(74) *Attorney, Agent, or Firm*—Millen, White, Zelano & Branigan, P.C.

(57) ABSTRACT

The invention relates to a method and an apparatus for the on-line analysis of liquid substance mixtures by means of NIRS. For evaluation by spectral data comparison, merely the binary mixtures of the possible components in quantitative graduations are used as calibration spectra. In order to accelerate the evaluation, all data points of a spectrum are summated, and each spectrum is characterized by only one characteristic number.

18 Claims, 3 Drawing Sheets

METHOD AND DEVICE FOR THE ONLINE ANALYSIS OF SOLVENT MIXTURES

The invention relates to a method for the on-line analysis of liquid substance mixtures by means of near infrared spectroscopy (NIRS), and to an apparatus for carrying out this method and to the use of this apparatus in regulated substance distribution devices.

In chemical production, waste in liquid form is produced daily. This is collected in the form of large batches in areas which have to be classified as explosion-risk zones. Owing to recent legislation regarding the handling of waste (German Circular Economy and Waste Act), solvent mixtures can be subjected to recovery, material recycling, energy recovery or disposal, depending on their composition, with the higher-value process having priority over disposal. Mixtures of spent solvents can be re-used directly or their components can be recovered if their composition meets certain criteria. In general, mixtures of this type should not have more than three components and should at most be weakly coloured or have a low level of contamination with coarse particles. Precise limits cannot be set owing to the wide variety of mixtures produced and the user- or recycler-specific acceptance criteria. If solvent mixtures are to be subjected to material recycling or returned to production, a detailed analytical result of the composition is a vital prerequisite. Analysis of the composition is also essential as goods-in or declaration inspection on delivery of solvent mixtures. The analysis must provide information on the qualitative and also the quantitative composition of the mixtures, otherwise only energy recovery and disposal remain as options.

For efficient substance stream management, the analysis of liquid substance mixtures should therefore generally meet the following requirements:

The measurement must be sufficiently quick that it does not delay the time taken to combine the individual containers to form large batches The measurement must be sufficiently quick that it does not delay the time taken to combine the individual containers to form large batches (i e. the measurement including evaluation should require less than 30 seconds).

The measurement must take place in the explosion-protection area.

Since the water content is a crucial parameter for the application or recycling method, quantitative determination of water must be possible.

Measurement in the gas phase at first appears appropriate for analysis of solvent mixtures since the interactions between mixture components are so weak there that they do not have to be taken into account in the measurement and in particular in the evaluation. Owing to the different vapour pressures of the components, the composition of a solvent mixture in the gas phase differs from that in the liquid phase. This is disadvantageous and requires subsequent correction calculations. A further disadvantage of measurement in the gas phase consists in the determination of the water content. In the gas phase, this can only be analysed under conditions which would require complex safety measures in the explosion-risk zone.

These disadvantages do not arise in the case of measurements in the liquid phase. Here, however, increased interactions between the components have to be taken into account.

One possibility for fast, qualitative or quantitative on-line analysis of solvent mixtures is near infrared spectroscopy (NIRS), which offers the following advantages.

Measurements are possible within seconds.

The use of quartz fibre optics which are transparent in the near infrared spectral region enables the spectrometer to be positioned outside the explosion-risk zone.

NIRS enables water to be determined quantitatively.

On use of NIRS for analytical problems, it is necessary firstly for spectra of "known" samples to be measured and filed in a reference database for calibration. Based on this database, spectra of "unknown" samples are then measured in routine operation, compared with the reference spectra in the database and accordingly evaluated qualitatively or quantitatively. In order to avoid incorrect results in this evaluation, the spectra of the samples that have been included in the reference database must cover at least the same variation latitude as the samples which are to be measured in routine operation and evaluated on the basis of the reference spectra.

Although NIRS has been used for on-line analysis in goods-in and production, it has not hitherto been employed for waste analysis since it has not been possible to use it for the simultaneous analysis of the type and proportion of the individual components in complex solvent mixtures of variable composition, without taking into account the declaration and without considerable calibration effort.

Mixtures of a plurality of solvents exhibit solvatochromic effects in the liquid phase, the extent of which are determined both by the type and the proportion of the individual components. These effects have been investigated for solutions of chromophoric substances as a function of various solvents. Data for mixtures of different solvents are rare. However, available data show that the solvatochromic interactions are very complex and can only be described or calculated systematically with difficulty. The creation of a database with reference spectra is therefore essential for calibration.

The test for the benefit of higher-value recycling methods as part of waste analysis comprises the recognition of, for example, at least 20 different solvents in mixtures, which may consist of 1, 2, 3 or 4 components. A database would have to include all possible combinations, i.e. count, and k is the number of components to be taken into account in a mixture.

In order to determine the quantitative composition and in order to take into account any solvatochromic effects, the percentage of components in the mixture, i.e. their quantitative graduation, must also be taken into account. This is calculated from $$\binom{s}{k}$$

where s is the number of quantitative graduations of k components. In accordance with the basic procedure described above for building up a reference database, the number of solvent mixtures to be calibrated for analysis of up to 4 of 20 components with a 10% quantitative graduation works out in accordance with these two formulae as 449 730. This number relates merely to the possible combinations of the pure solvents which are to be expected in routine operation. Additional variations in the solvent mixtures to be taken into account, for example in the form of particulate or coloured impurities, would further increase this number significantly. The recording of such a number of reference spectra is clearly not sensible.

The use of factorial experiment plans for calculating the minimum numbers of calibration and reference samples required is known, but these cannot be used sensibly for systems which are defined by interactions and which are to be characterised qualitatively and quantitatively at the same time.

In addition, a further problem arises in the evaluation of the spectra. A known method is principal component analysis (PCA), which, although based on all the information in a spectrum, reduces this to a few principal components, known as factors, which represent the most important information for the analytical differentiation desired. The remainder of the information is collected in a so-called residue. This makes it possible to make "yes/no" statements, but not to make quantitative statements and to assess "outliers". Quantitative evaluation by means of principal component regression (PCR) or partial least squares regression (PLSR) requires knowledge of the identity of the substances to be investigated.

The only method hitherto that uses all the spectral information without data reduction is direct spectral matching. The disadvantage of this spectra comparison method is the high demand for computer resources for repeated comparative calculation of all data points of the measured and reference spectra.

The object is thus to reduce the calibration effort and simplify the evaluation in order that NIRS can also be used for waste analysis. A further object is to provide a measurement apparatus, i.e. an NIR spectrometer with additional modules which are necessary in accordance with the invention, for methods of this type.

It has been found that it is possible to restrict the compilation of a reference database for calibration to the binary combinations of the solvents to be taken into account.

It has furthermore been found that, in order to accelerate the searching of the database, each full spectrum can be characterised by only a single characteristic number.

The invention therefore relates to a method for the analysis of liquid substance mixtures by NIRS, in which the solvatochromic effects of the mixture as a whole are approximated by the solvatochromic effects of the two-component mixtures present therein. To this end, a calibration database is compiled which contains, as reference spectra, the binary mixtures of all possible solvents in predefined quantitative graduations.

A preferred embodiment of the method according to the invention is calibration with two-component mixtures in 2–10% predefined quantitative graduations.

A further preferred embodiment of the method according to the invention is calibration with two-component mixtures in predefined, non-equidistant, quantitative graduations.

A preferred embodiment of the method according to the invention is calculation of spectra representing 3 and 4 components by additive linear combination of the two-component mixture spectra present in the database taking into account the proportions, which can either be carried out by multiplication by coefficients of between 0 and 1 before the combination, where the sum of the coefficients gives 1 in total, or by division after the combination, where the divisor is given by the number of two-component mixture spectra that have been combined.

A further preferred embodiment of the method according to the invention is evaluation by comparison of the spectral data, where the full spectra are compared directly with one another.

A possible embodiment of the method according to the invention is data compression of the full spectra by forming the product of the spectral data points and the associated wavenumbers for each spectrum, and summation via the modified data points obtained therefrom. On use of this method for accelerating searching of the database by protecting computer resources, the result of the search should be checked by comparison of the full spectra.

A further possible embodiment is data compression of the full spectra by translation into a number sequence which encodes the characteristic shape of a spectrum in shortened form by summation of the rising and falling spectral data points in each case following one another by lining up the respective part-sums.

The invention furthermore relates to a measurement apparatus for the measurement and evaluation of NIR spectra, comprising an NIR spectrophotometer having a light source, a monochromator, a measurement cell and a radiation receiver, with a data processing unit being provided which takes data from the said NIR photometer and which has a comparison data-base containing binary NIR reference spectra, and a module for comparison of a measured spectrum with the said reference spectra.

A possible embodiment is the additional use of a data compression module, which characterises the reference spectra and measured spectra by means of characteristic numbers, it being possible to calculation these characteristic numbers by the said possible embodiments of the method according to the invention for data compression.

A further possible embodiment is a measurement apparatus in which the said comparison database additionally contains data sets for multicomponent mixtures.

The invention furthermore relates to the use of a measurement apparatus of this type in a regulated apparatus for the distribution of fluid components. Finally, the invention also relates to regulated apparatuses for substance distribution in which a measurement apparatus according to the invention serves as actual-value transmitter.

Figure 1:
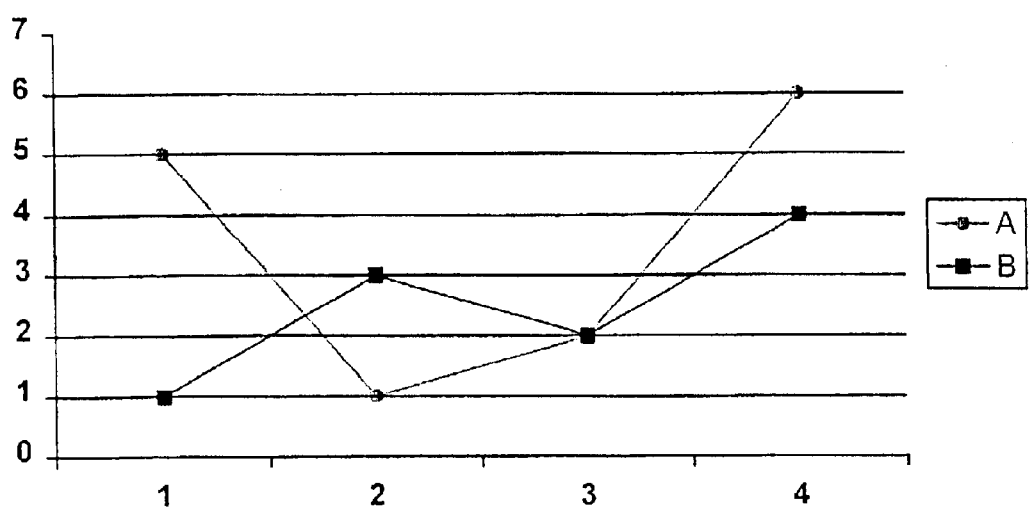
FIG. 1 shows an X/Y coordinate system with a graphical representation of two data sets (spectra).

Spectrometers for NIR measurement are known in the prior art. Such photometers typically have a cell, which may, for example, be designed as a flow cell, furthermore a light source, a monochromator, a radiation receiver, a signal amplification and signal evaluation device, and optionally a control device. In further apparatus variants known in the prior art, a plurality of light sources and/or radiation receivers with corresponding switching devices are provided. As is known, photometers can be constructed in accordance with the single-beam or twin-beam principle. Equipment variants of this type are familiar to the person skilled in the art.

The spectra recorded by the spectrometer represent the light flux weakened by a measured sample or changed sample-specifically. The spectra are composed of the totality of individual spectral data points, the number of which depends both on the wavelength range used for the measurements and on the resolution of the spectrometer optical system. These spectral data points obtained by means of transmission, reflection or transflection measurement are typically represented in the form of absorption or transmission spectra. The transmission defines what fraction of the incident light intensity $I_0$ leaves the sample again ($T=I/I_0$). The absorption corresponds to the decimal logarithm of the reciprocal of the transmission ($A=\log_{10} 1/T$). The various variants for the measurement of spectra and representation of spectral data points are known to the person skilled in the art.

The measurement apparatus provided in accordance with the invention additionally has modules which are necessary for the method described below. These include a comparison database, optionally a data reduction module, and a comparison device in order to compare the measured spectra, if desired using the data reduction module, with the spectra in the comparison database, to select the spectrum from the comparison database which is the most similar to the measured spectrum and to indicate the composition of the substance mixture which corresponds to the spectrum selected from the comparison database.

The method according to the invention can in principle be employed for all analytical problems in which liquid, semi-solid and/or solid mixtures consisting of two or more components are to be evaluated qualitatively and/or quantitatively. Areas of application may be, for example, goods-in inspection, process control, quality control or waste analysis.

The method according to the invention may in addition also be employed for all analytical problems in which solutions of dissolved substances in solvents and solvent mixtures are to be evaluated qualitatively and/or quantitatively. Areas of application here may also be, for example, goods-in inspection, process control, quality control or waste analysis.

Data compression by means of the said encoding of spectra by numerical sequences as a possible embodiment of the method according to the invention can in principle be employed for all analytical problems in which extensive data sets are handled and processed. Areas of application may be, for example, control and optimisation methods in goods-in inspection, process control, quality control or waste analysis.

In waste analysis, the specific requirement is the analysis of liquid multicomponent systems. By means of the method according to the invention, preferably mixtures of up to 4 components from 20 possible components are analysed, it being possible to increase the number of possible components and the components to be analysed therefrom if the spectra database according to the invention is expanded. The chemical interactions which characterise the spectrum of a mixture consisting of a plurality of components, depending on their nature and proportion, can be interpreted to an approximation as the sum of the part-contributions of all binary interactions in this mixture. It is thereby possible for the compilation of the database to be restricted to the binary combinations of the solvents to be taken into account.

For all possible binary combinations, a calibration data set is set up which contains the comparison spectra of the respective binary mixtures in various compositions, i.e. percentage or quantitative graduations. The finer the graduations, the more comparison spectra have to be produced. Depending on the specific requirements regarding the qualitative and especially quantitative accuracy of the method, the percentage graduation should be between 1 and 20%, preferably between 2 and 10%, particularly preferably between 5 and 10%. In order to compensate for base-line shifts, which are to be expected in routine operation due to particulate impurities, the spectra are subjected to standardisation and base-line correction before calculation of the characteristic numbers.

Evaluation by comparison of the full spectra or by comparison of characteristic numbers which can be obtained on the basis of the full spectra by data compression modules means that the method is not restricted to the use of an equidistant calibration data set. In areas of relatively great use or recycling relevance, more accurate quantitative information can be obtained by the introduction of narrower percentage graduations without the unequal weighting of the calibration data falsifying the information. It is thus advisable, for example, in waste analysis for the detection of substances whose proportion is less than 10%, to select the percentage graduation more narrowly in such peripheral regions. In addition to an equidistant 10% graduation over the entire range, binary mixtures, for example, with 3, 6 and 9% of the respective first solvent could be included in the calibration database.

In order to compile a database for the analysis of mixtures of 20 solvents to be taken into account, all that is needed in the method according to the invention is to record all possible binary combinations, for example with a linear quantitative graduation of 10%. This corresponds to 1710 solvent mixtures to be calibrated. Compared with the number of 449 730 mixtures which would have to be measured without the restriction according to the invention, this means a reduction in the amount of data required of 99.6%. Compression of the full spectra by the method according to the invention allows an additional data reduction of up to 99%, based on a spectrum with 100 data points. With an increasing number of data points, the reduction factor can also increase correspondingly. Binary mixtures which cannot be prepared owing to large differences in polarity of their components, but instead occur as two-phase mixtures, are not included in the database. The mixtures to be analysed should therefore be checked in advance in order that only single-phase mixtures are sent to NIR analysis.

If a third component serves as solubiliser for the two other, normally immiscible components, the only interactions that occur in the mixture are those with the solubiliser. Interactions between immiscible components do not occur either in complex mixtures, and consequently the absence of these binary combinations in the spectral database does not have an adverse effect.

A measurement apparatus according to the invention thus comprises a comparison database which contains at least the data sets of all binary combinations taking into account the quantitative graduations proposed.

In the preferred embodiment of the method according to the invention, mixtures of 3 or more components are not part of the database. They are simulated by the search algorithm on comparison between the currently measured spectrum and the database spectra by linear combination of the binary spectra. The selection of the spectra used for the simulation depends on the degree of agreement with the spectrum of the mixture to be analysed.

The measurements are preferably evaluated by direct comparison of the full spectra. To this end, each data point is compared individually between the respective measured spectrum to be analysed and the reference spectra present in the database.

A possible embodiment for evaluation of the measurements is data compression of the full spectra both for the respective measured spectrum to be analysed and also for the reference spectra present in the database. The reduction in the computer capacity necessary for repeated point-to-point comparison of the full spectra thus enables the speed of database searching to be increased.

Consequently, the comparison database mentioned can contain the measured full spectra and/or the characteristic numbers determined in accordance with the invention.

In this way, liquid multicomponent mixtures can for the first time be analysed qualitatively and quantitatively at the same time in a few seconds by means of NIRS, independently of prior information. The new formulations for spectral data compression are generally advantageous if extensive databases have to be searched for agreement with a data set to be characterised (for example spectrum) or differences between data sets are to be determined. In addition to waste analysis, this is the case, for example, in on-line monitoring of solvent filling lines or characterisation of substances such as medicaments in production or quality control.

General explanations regarding the preferred procedure in:
1. Searching of the spectra database
2. Calculation of the characteristic numbers 1. Searching of the Spectra Database:

The spectral comparison is based on the following general principle: Comparison between X/Y curves. The separation between the curves serves as assessment criterion for agreement. To this end, the following prior conditions should be satisfied:
1. Define X values (spectral range used, spectral resolution);
2. Determine Y values (measurement of the database spectra, measurement of the spectra to be compared);
3. Scaling of the curves to be compared by means of standardisation, base-line correction or other known suitable methods.

The comparison between a measurement spectrum to be analysed and the reference spectra in the database is carried out, in the preferred embodiment, in accordance with the following scheme:
1. Definition of the wavelength scale and pretreatment method for the database and measured spectra, calculation of the characteristic numbers for the database spectra;
2. Measurement of the spectrum of an unknown substance mixture (X);
3. Selection of the wavelength scale and pretreatment method for the spectrum X as in point 1, calculation of the characteristic numbers,
4. Comparison of the measured spectrum X with the database spectra of the pure solvents:

X=>A, B, C, D, E, F, G, H, I, J, K, L, M, N, O, P, Q, R, S, T
5. Selection of 10 solvents with the best agreement with the measured spectrum X;
(Example: A, B, C, D, E, F, G, H, I and J)
6. Selection from the database of all two-component mixtures which consist of the 10 solvents selected;
7. Comparison of the measured spectrum X with these two-component mixtures;

X=>AB, AC, AD, AE, AF, AG, AH, AI, AJ
BC, BD, BE, BF, BG, BH, BI, BJ
CD, CE, CF, CG, CH, CI, CJ
DE, DF, DG, DH, DI, DJ
EF, EG, EH, EI, EJ
FG, FH, FI, FJ
GH, GI, GJ
HI, HJ
IJ

8. Calculation of all possible three-component mixtures with reference to the two-component mixtures selected under point 6. The calculation is carried out, for example, for the three-component mixture ABC in accordance with:

$$ABC = \frac{\sum AB + AC + BC}{q}$$

q=number of two-component mixtures required for the calculation.

The divisor q can also be integrated in each case into a coefficient before the two-component mixture spectra.

The quantitative composition of a three-component mixture ABC calculated in this way is obtained as follows:
(The lines represent the two-component mixture spectra selected from the database, the columns their quantitative composition).

|  | A | B | C |  |
|---|---|---|---|---|
| AB | 70% | 30% |  |  |
| AC | 50% |  | 50% |  |
| BC |  | 30% | 70% |  |
| Totals: | 120% | 60% | 120% | /q |
| Result: A:B:C |  | 40%:20%:40% |  |  |

9. Comparison of the measured spectrum X with the three-component mixtures calculated as described under point 8.

X=>ABC, ABD, ABE, ABF, ABG, ABH, ABI, ABJ
ACD, ACE, ACF, ACG, ACH, ACI, ACJ
ADE, ADF, ADG, ADH, ADI, ADJ
AEF, AEG, AEH, AEI, AEJ
AFG, AFH, AFI, AFJ
AGH, AGI, AGJ
AHI, AHJ
AIJ
. . . correspondingly for all further possible combinations;

10. Calculation of all possible four-component mixtures with reference to the two-component mixtures selected under point 6. The calculation is carried out, for example, for the four-component mixture ABCD in accordance with:

$$ABCD = \frac{\sum AB + AC + AD + BC + BD + CD}{q}$$

11. Comparison of the measured spectrum X with the four-component mixtures calculated under point 10 (diagrammatic representation as in point 7 and point 9);
12. As the end result, the best overall agreement determined in the comparative calculations under points 4, 7, 9 and 11 is output.

The apparatus according to the invention thus furthermore comprises a module which facilitates the comparison methods described above. The implementation of comparison methods of this type and details for their programming are known to the person skilled in the art.

A further possible embodiment proposes calculating all possible three-, four- or multicomponent mixtures once with reference to the two-component mixture spectra and additionally including them in the database. In this way, points 8 and 10 mentioned above are unnecessary on comparison with a measured spectrum X, which can simplify and thus accelerate the algorithm mentioned above. Alternatively, the advance selection mentioned under point 5 can also then be omitted, and the entire database searched for the database spectrum which agrees best with the measured spectrum X. It is thus possible to avoid a substance present in the measured spectrum X possibly not being recognised by the advance selection.

The comparison database used in accordance with the invention can thus also contain the data for ternary or quaternary mixtures in addition to the data for binary mixtures. In this case, the comparison database may, as mentioned above, contain the full spectra and/or the characteristic numbers determined in accordance with the invention.

2. Calculation of the Characteristic Numbers:

In order to accelerate the spectra database searching mentioned under point 1, characteristic numbers can be used instead of the differences summated over all data points. The figures used for assessment of the spectral comparison thus arise from the differences in the characteristic numbers of the spectra to be compared. In a possible embodiment of the method according to the invention, the characteristic numbers of a spectrum represent the summated products from the wavenumbers (X values) and the associated spectral data points (Y values). The procedure for calculating the characteristic numbers is explained with reference to the following scheme:

The X/Y coordinate system is shown by the graphical representation of two data sets (spectra). A corresponding representation is also found in FIG. 1:

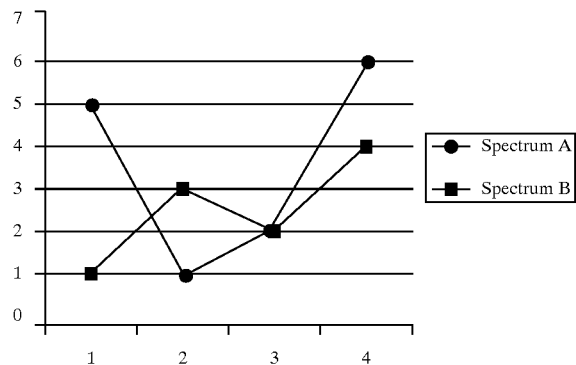

The table lists the values (spectral data points) from the above graphical representation:

| Wavelength | Measured values (A) | Measured values (B) | Difference (A − B) | Product (A*) | Product (B*) | Difference (A* − B*) |
|---|---|---|---|---|---|---|
| 1 | 5 | 1 | 4 | 5 | 1 | 4 |
| 2 | 1 | 3 | −2 | 2 | 6 | −4 |
| 3 | 2 | 2 | 0 | 6 | 6 | 0 |
| 4 | 5 | 4 | 2 | 24 | 16 | 8 |
| Column total: | 14 | 10 | 4 | 37 | 29 | 8 |

A* and B* indicate the product of the respective measured value and the corresponding wavelength.

The same result is obtained irrespective of whether firstly the difference between the products A* and B* is calculated row by row and then summated or firstly the products for each of A* and B* are summated and the difference is then calculated.

This means that, with the aim of accelerated database searching on comparison between a newly measured spectrum of an unknown substance mixture (spectrum B) and a database spectrum (spectrum A), it is unnecessary repeatedly to calculate and then summate the differences between the individual spectral data points. Against this background, the characteristic numbers calculated separately for all reference spectra can be included in the database, reducing the calculation effort for each subsequent comparison with a newly measured spectrum of an unknown substance mixture to a once-only calculation of the characteristic number for this spectrum and repeated comparison with the database spectra characteristic numbers already present in the database.

Since the wavenumbers in infrared spectra are generally a few powers of ten greater than the associated spectral data points, the wavenumbers should be scaled before the product calculation in order that they can be compared by multiplication by a suitable coefficient of the spectral data points to the power ten.

The reference spectra determined from the comparison of the characteristic numbers from the database generally only represent a preliminary selection. In order to safeguard against false-positive results, the result of the database search accelerated by this method should be checked at the end of the search by direct comparison of the spectral data points of the respective measured spectrum to be analysed with the reference spectra selected after the database search, since smaller wavenumbers with larger values of the associated spectral data points can give the same contribution to the characteristic numbers as larger wavenumbers with smaller values of the associated spectral data points. The difference between two full spectra would be large in such a case, but the difference between their characteristic numbers would be small.

It is also possible to carry out optimisations by subjecting the database spectra and, in the same manner, the respective measured spectra to be compared to a suitable mathematical pretreatment method before a direct comparison of these full spectra or a data compression method and comparison with reference to the characteristic numbers obtained is carried out. This optimisation can serve to emphasise particular spectral characteristics and to suppress interfering spectral characteristics.

A possible optimisation before the characteristic numbers calculation proposes, for example, the following procedure:

1. Performance of a top-hat transformation in accordance with the general formula $$M_i^* = M_i - \left(\frac{M_{i-1} + M_{i+1}}{2}\right)$$

$M_i^*$ = transformed measured value $M_i$ = measured value $i$ = index of the measured value;

2. Selection of peaks of a certain size, multiplication of the values for the spectral data points for these peaks by the associated wavenumbers in accordance with the said scaling;
3. Addition of the values obtained from point 2 for the original spectrum;

calculation of the characteristic number in accordance with the procedure described above.

The said transformation method enables optimisation before the direct comparison of full spectra without using data reduction modules.

A further embodiment of the characteristic number calculation for data compression as a possible constituent of the method according to the invention and accelerated database search comprises encoding the respective curve shapes of the measured spectra and the spectra used as reference by summation of the decreasing and increasing spectral data points in each case following one another and lining up the respective part-sums as numerical sequences.

If the spectral data points of a spectrum, starting from the 1st wavenumber, show, for example, a curved shape in which the values of the spectral data points decrease up to the 4th wavenumber, increase up to the 10th wavenumber, decrease up to the 14th wavenumber and increase again up to the 20th wavenumber, the lined-up part-sums for the decreasing and increasing values in each case following one another (3-6-3-6) show the numerical sequence 3636.

It must be defined in advance whether the first number encodes the first decreasing or the first increasing sequence of values of a spectrum. Differences between measured spectra and the reference spectra present in the database, all of which are subjected to this data compression method, are thus evident both in the length of the respective numerical sequences and in differences between the numbers at the individual positions of the sequence.

The method features described in detail and the information given in connection therewith for implementing this method in a measurement apparatus enable the person skilled in the art to produce programming and a database structure which are suitable for carrying out the method according to the invention and thus to provide the measurement apparatus according to the invention.

The programmes and databases necessary for the method according to the invention can either be implemented in addition to the data processing unit serving for control and regulation during the NIRS measurement, or it is likewise possible to implement these programmes and databases on a separate data processing unit; this additionally provided data processing unit contains the data in accordance with known data transfer protocols of the data processing unit of the NIR spectrophotometer.

Such a measurement apparatus according to the invention can also be used as actual-value transmitter in a regulated apparatus for substance distribution. Thus, for example, a fluid stream can be introduced into various containers under automatic control in accordance with the composition.

Even without further details, it is assumed that a person skilled in the art will be able to utilise the above description in its broadest scope. The preferred embodiments and examples should therefore merely be regarded as descriptive disclosure which is absolutely not limiting in any way.

The complete disclosure content of all applications, patents and publications mentioned above and below, in particular the corresponding application DE 199 63 561, filed on 23 Dec. 1999, is incorporated in this application by way of reference.

EXAMPLES

Example 1

Compilation of a Database

The database is to contain binary mixtures of 20 different solvents (see table) in a 10% quantitative graduation.

To this end, the binary mixtures were mixed from the pure solvents by means of an HPLC pump and measured in through-flow in a 375 µl quartz cell with a layer thickness of 5 mm.

| methanol | ethanol | acetonitrile |
| acetone | 2-propanol | diethyl ether |
| tert-butanol | dichloromethane | MTB ether |
| ethyl acetate | n-hexane | chloroform |
| tetrahydrofuran | xylene | cyclohexane |
| n-heptane | pyridine | toluene |
| petroleum ether | water | |

The spectra obtained were subsequently subjected to database data compression according to the invention.

Example 2

Analysis of an Unknown Mixture

Figure 2:
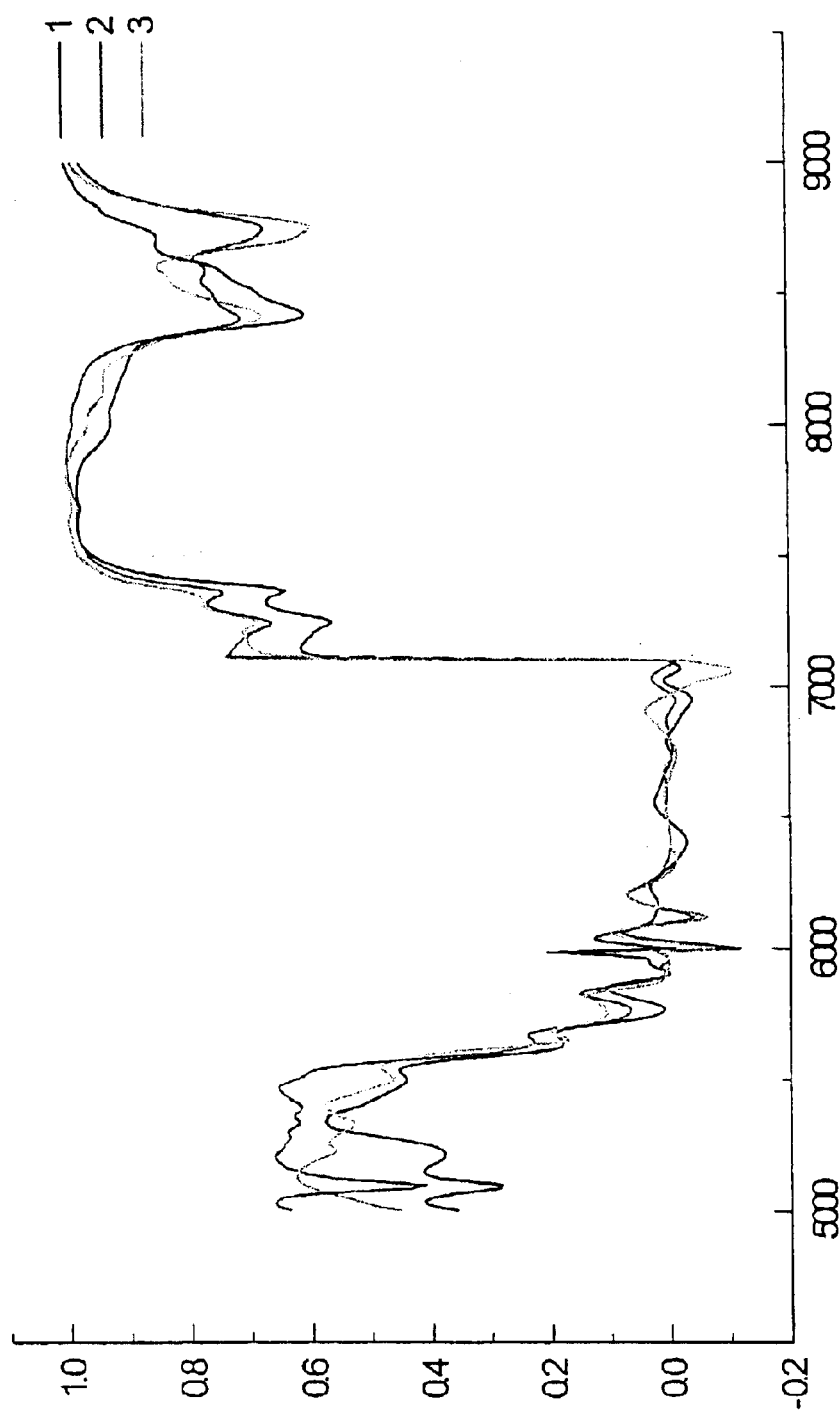
FIGS. 2 and 3 are explained in greater detail in Example 2.
Figure 3:
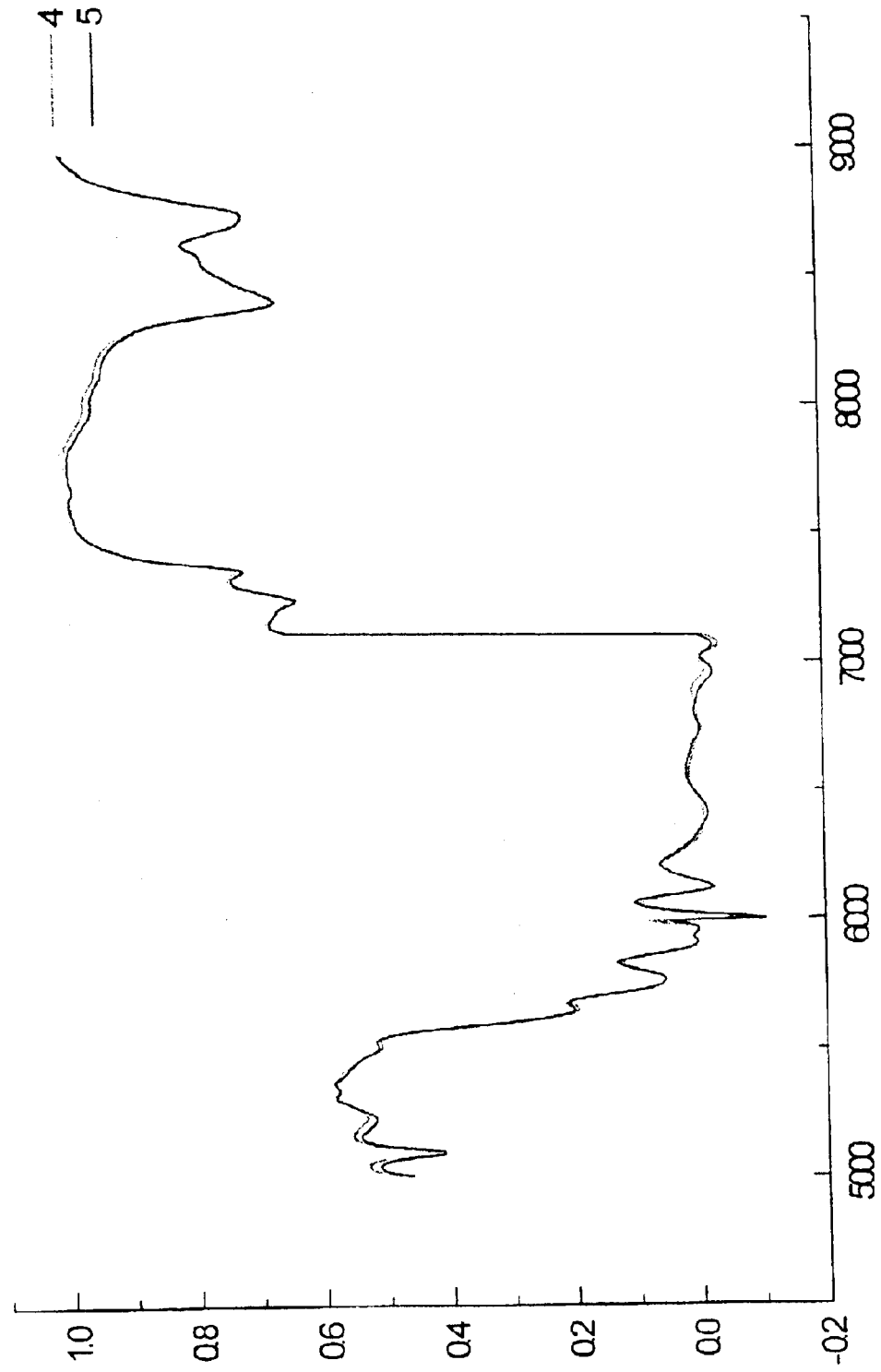

FIGS. 2 and 3 show the procedure for searching the spectra database with reference to a practical example.

FIG. 2 shows the spectra of the two-component mixtures acetone:isopropanol 70:30 (curve 1), acetone:toluene 50:50 (curve 2) and isopropanol:toluene 30:70 (curve 3) present in the database. FIG. 3 shows the three-component mixture spectrum acetone:isopropanol:toluene 40:20:40 (curve 4) calculated by the method according to the invention from the spectra from FIG. 2 and the three-component mixture spectrum acetone:isopropanol:toluene 40:20:40 (curve 5) actually measured.

Wavenumbers in $cm^{-1}$ are plotted on the abscissae and the measured spectral data points (shown as transmission values) at the respective wavenumbers are plotted on the ordinates.

What is claimed is:

1. A method for on-line analysis of the solvent content of a liquid substance mixture comprising at least two solvents, the method comprising obtaining a near infrared measured spectrum of said mixture and comparing said spectrum with a calibration database that contains near infrared spectral data on binary mixtures of solvents which could be present in said mixture in predefined quantitative graduations that are in the range between 2 and 10%.

2. A method for on-line analysis of the solvent content of a liquid substance mixture comprising at least two solvents, the method comprising obtaining a near infrared measured spectrum of said mixture and comparing said spectrum with a calibration database that contains near infrared spectral data on binary mixtures of solvents which could be present in said mixture in predefined quantitative graduations that are not equidistant.

3. A method for on-line analysis of the solvent content of a liquid substance mixture comprising at least two solvents, the method comprising obtaining a near infrared measured spectrum of said mixture and comparing said spectrum with a calibration database that contains near infrared spectral data on binary mixtures of solvents which could be present in said mixture in predefined quantitative graduations, and further comprising calculating spectral data for 3 or 4 component mixtures by additive linear combination of the two-component mixture spectral data present in the database, where the additive linear combination is performed by a calculation that weighs the contribution of each spectral data on binary mixtures in the calculated spectral data for the 3 or 4 component mixtures.

4. A method for on-line analysis of the solvent content of a liquid substance mixture comprising at least two solvents, the method comprising obtaining a near infrared measured spectrum of said mixture and preparing characteristic numbers for the spectrum by selecting a set of spectral data points which are measured spectral values at predefined wavelengths and obtaining the products of the spectral data points with the corresponding wavelengths and comparing said characteristic numbers with a calibration database that contains characteristic numbers on binary mixtures of solvents which could be present in said mixture in predefined quantitative graduations.

5. A method according to claim 4, wherein comparing the characteristic numbers obtained from the measured spectrum with the characteristic numbers in the database is accomplished by calculating the differences between the characteristic numbers obtained from the measured spectrum and the corresponding characteristic numbers in the database.

6. A method according to claim 1, wherein comparing the measured spectrum with the calibration database that contains spectral data on binary mixtures is accomplished by generating a numerical sequence based on the measured spectrum and comparing the numerical sequence with number sequence data in the calibration database, wherein the numerical sequence is obtained by ascertaining the slope of the curve representing measured spectral values at predefined wavelengths, wherein the first number in the sequence represents the number of sets until the sign of the slope of the curve changes, and each subsequent number in the sequence represents the number of sets until the sign of the slope changes again.

7. A method according to claim 1, further comprising compiling a database that contains spectral data on binary mixtures of solvents.

8. A method according to claim 2, further comprising compiling a database that contains spectral data on binary mixtures of solvents.

9. A method according to claim 3, further comprising compiling a database that contains spectral data on binary mixtures of solvents.

10. A method according to claim 4, further comprising compiling a database that contains spectral data on binary mixtures of solvents.

11. A method according to claim 1, further comprising calculating spectral data for 3 or 4 or more component mixtures by additive linear combination of the two-component mixture spectral data present in the database, where the additive linear combination is performed by a calculation that weighs the contribution of each spectral data on binary mixtures in the calculated spectral data for the 3 or 4 of more component mixtures, and saving the spectral data for 3 or 4 or more component mixtures in the database.

12. A method according to claim 11, further comprising using the spectral data for 3 or 4 or more component mixtures in the database as reference spectral for evaluating 3 or 4 or more component mixtures.

13. A method according to claim 6, further comprising saving the characteristic number data in the database.

14. A method according to claim 13, further comprising using the characteristic number data in the database as reference data for evaluating characteristic number data for a measured mixture.

15. A method according to claim 1, wherein comparing the measured spectrum with the calibration database that contains spectral data on binary mixtures is accomplished by calculating the differences between the measured spectral data values and the spectral data in the database.

16. A method according to claim 2, wherein comparing the measured spectrum with the calibration database that contains spectral data on binary mixtures is accomplished by calculating the differences between the measured spectral data values and the spectral data in the database.

17. A method according to claim 3, wherein comparing the measured spectrum with the calibration database that contains spectral data on binary mixtures is accomplished by calculating the differences between the measured spectral data values and the spectral data in the database.

18. A method according to claim 4, wherein comparing the characteristic numbers obtained from the measured spectrum with the characteristic numbers data in the database is accomplished by a) calculating the differences between the characteristic numbers obtained from the measured spectrum and the corresponding characteristic numbers in the database and summing these values to obtain a single characteristic number, or b) summing the characteristic numbers obtained from the measured spectrum and also summing the corresponding characteristic numbers in the database and calculating the difference between these values to obtain a single characteristic number.

* * * * *

UNITED STATES PATENT AND TRADEMARK OFFICE
CERTIFICATE OF CORRECTION

PATENT NO. : 6,820,013 B1
DATED : November 16, 2004
INVENTOR(S) : Hans Frickel

It is certified that error appears in the above-identified patent and that said Letters Patent is hereby corrected as shown below:

<u>Title page</u>,
Item [86], PCT No.,
§ 371 (c)(1),
(2), (4) Date, reads "Oct. 16, 2000" should read -- Oct. 16, 2002 --

Signed and Sealed this

Third Day of May, 2005

JON W. DUDAS
*Director of the United States Patent and Trademark Office*